(12) United States Patent
Bennett et al.

(10) Patent No.: US 7,708,693 B2
(45) Date of Patent: May 4, 2010

(54) SYSTEM AND METHOD FOR DETECTING ARTIFACTUAL HEMODYNAMIC WAVEFORM DATA

(75) Inventors: Tommy D. Bennett, Shoreview, MN (US); Mark Choi, Mississauga (CA); David A. Igel, Lino Lakes, MN (US); Michael R. S. Hill, Minneapolis, MN (US); Teresa A. Whitman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 1499 days.

(21) Appl. No.: 11/044,618

(22) Filed: Jan. 27, 2005

(65) Prior Publication Data

US 2006/0167360 A1 Jul. 27, 2006

(51) Int. Cl.
*A61B 5/02* (2006.01)
(52) U.S. Cl. .............. 600/485; 600/481; 600/483; 600/500
(58) Field of Classification Search ............. 600/481, 600/483–486, 488, 490–504, 508–528, 300, 600/301, 561
See application file for complete search history.

(56) References Cited

U.S. PATENT DOCUMENTS

| | | | | |
|---|---|---|---|---|
| 4,870,973 A | * | 10/1989 | Ueno | 600/493 |
| 4,974,597 A | * | 12/1990 | Walloch | 600/493 |
| 5,267,567 A | * | 12/1993 | Aung et al. | 600/493 |
| 5,368,040 A | | 11/1994 | Carney | |
| 5,392,781 A | * | 2/1995 | Phillipps et al. | 600/493 |
| 5,417,717 A | | 5/1995 | Salo et al. | |
| 5,564,434 A | | 10/1996 | Halperin et al. | |
| 5,653,241 A | * | 8/1997 | Harada et al. | 600/493 |
| 5,865,756 A | * | 2/1999 | Peel, III | 600/490 |
| 5,895,359 A | * | 4/1999 | Peel, III | 600/494 |
| 5,931,790 A | * | 8/1999 | Peel, III | 600/494 |
| 6,007,492 A | * | 12/1999 | Goto et al. | 600/485 |
| 6,104,949 A | | 8/2000 | Pitts Crick et al. | |
| 6,155,267 A | | 12/2000 | Nelson | |
| 6,258,037 B1 | * | 7/2001 | Dowling, Jr. | 600/493 |
| 6,275,707 B1 | | 8/2001 | Reed et al. | |
| 6,280,409 B1 | | 8/2001 | Stone et al. | |
| 6,283,922 B1 | * | 9/2001 | Goto et al. | 600/485 |
| 6,309,350 B1 | | 10/2001 | VanTassel et al. | |
| 6,332,867 B1 | * | 12/2001 | Chen et al. | 600/300 |
| 6,347,245 B1 | * | 2/2002 | Lee et al. | 600/523 |
| 6,438,408 B1 | | 8/2002 | Mulligan et al. | |
| 6,527,726 B2 | * | 3/2003 | Goto et al. | 600/485 |
| 6,602,199 B2 | * | 8/2003 | Chen et al. | 600/485 |
| 6,610,017 B2 | * | 8/2003 | Oka | 600/485 |
| 6,730,038 B2 | * | 5/2004 | Gallant et al. | 600/485 |
| 6,827,688 B2 | * | 12/2004 | Goto et al. | 600/485 |

(Continued)

OTHER PUBLICATIONS

Schram, "Differential Distribution of Cardiac Ion Channel Expression as a Basis for Regional Specialization in Electrical Function," Circ. Res. 2002; 90:939-50.

(Continued)

*Primary Examiner*—Charles A Marmor, II
*Assistant Examiner*—Navin Natnithithadha
(74) *Attorney, Agent, or Firm*—Stephen W. Bauer

(57) ABSTRACT

A system and method for cardiovascular analysis includes an implantable medical device capable of generating hemodynamic pressure waveform data based upon sensed pressure. Hemodynamic waveform data is analyzed to identify artifactual data represented in the hemodynamic waveform.

16 Claims, 11 Drawing Sheets

U.S. PATENT DOCUMENTS

| | | | |
|---|---|---|---|
| 7,016,721 B2 * | 3/2006 | Lee et al. | 600/523 |
| 7,048,691 B2 * | 5/2006 | Miele et al. | 600/504 |
| 2001/0037068 A1 * | 11/2001 | Goto et al. | 600/485 |
| 2002/0147401 A1 * | 10/2002 | Oka | 600/490 |
| 2003/0149369 A1 * | 8/2003 | Gallant et al. | 600/485 |
| 2003/0199779 A1 | 10/2003 | Muhlenberg et al. | |
| 2004/0167410 A1 | 8/2004 | Hettrick | |

OTHER PUBLICATIONS

Nerbonne, "Molecular Basis for Funcational Voltage-Gated K+ Channel Diversity in the Mammalian Myocardium," J Physiol. 2000; 525:285-98.

Heise, "Characterization of the Human Cysteinyl Leukotriene 2 Receptor," J. Biol. Chem., 2000; 275:30531-6.

Miake, "Biological Pacemaker Created by Gene Transfer," Nature, 418(12), pp. 132-133, 2002.

* cited by examiner

SYSTEM AND METHOD FOR DETECTING ARTIFACTUAL HEMODYNAMIC WAVEFORM DATA

BACKGROUND OF THE INVENTION

The present invention relates to a system and method for detecting and handling artifactual data in hemodynamic waveforms.

It is possible to obtain cardiovascular data, for healthcare and research purposes, using an implantable medical device (IMD) such as an implantable hemodynamic monitor (IHM), together with a pressure sensor lead that senses blood pressure within a heart chamber and an electrogram (EGM) of the heart. The IHM senses absolute blood pressure values, and the patient is also provided with an externally worn atmospheric pressure reference monitor record contemporaneous atmospheric pressure values.

A cardiovascular analysis system using the IHM can be programmed to sense and calculate various hemodynamic parameters. The IHM is programmed and interrogated employing an external programmer or a PC to accumulate trend data at a programmable resolution.

The memory buffers of the IHM and the atmospheric pressure reference monitor can transmit by telemetry the sensed and stored pressure and other data, thereby emptying the buffers, to a nearby interactive remote monitor for temporary storage of the data. The interactive remote monitor periodically transmits accumulated data to a remote data processing center that can process the data to develop trend data that the attending physician can review, along with other patient data derived in patient examinations and interviews, to assess cardiovascular health.

Such an IHM system implanted in patients suffering from adverse cardiovascular health conditions can accumulate date-stamped and time-stamped blood pressure data that can be of use in determining the condition of the heart and or vascular system over an extended period of time and while the patient is clinically tested or is engaged in daily activities. Various other IHM functions and uses of EGM, pressure and other parameter data accumulated in an IHM are disclosed in U.S. Pat. Nos. 5,368,040, 5,417,717, 5,564,434, 6,104,949, 6,155,267, 6,280,409, 6,275,707, 6,309,350, and 6,438,408, and U.S. Pat. App. Ser. Nos. 2003/0199779 and 2004/0167410.

Data collected by an IHM system may contain undesired artifactual data, in addition to desired data. Generally, artifactual data is any data corresponding to an inaccurate observation, effect, or result, especially one resulting from characteristics of the IHM system used in gathering the data or due to data collection error.

BRIEF SUMMARY OF THE INVENTION

The present invention relates to a cardiovascular analysis system that includes an implantable medical device that generates hemodynamic pressure waveform data based upon the hemodynamic pressure sensed. Hemodynamic waveform data is analyzed to identify artifactual data represented in the hemodynamic waveform, so that the artifactual data does not result in an inaccurate representation of a patient's health.

The invention also includes a method of hemodynamic waveform data analysis that includes sensing a hemodynamic pressure for a pulse cycle using an implantable medical device, generating hemodynamic pressure waveform data that represents the hemodynamic pressure as a function of time for the pulse cycle, and analyzing the hemodynamic pressure waveform data to determine if artifactual waveform data is present in the hemodynamic waveform data.

DETAILED DESCRIPTION

Figure 1:
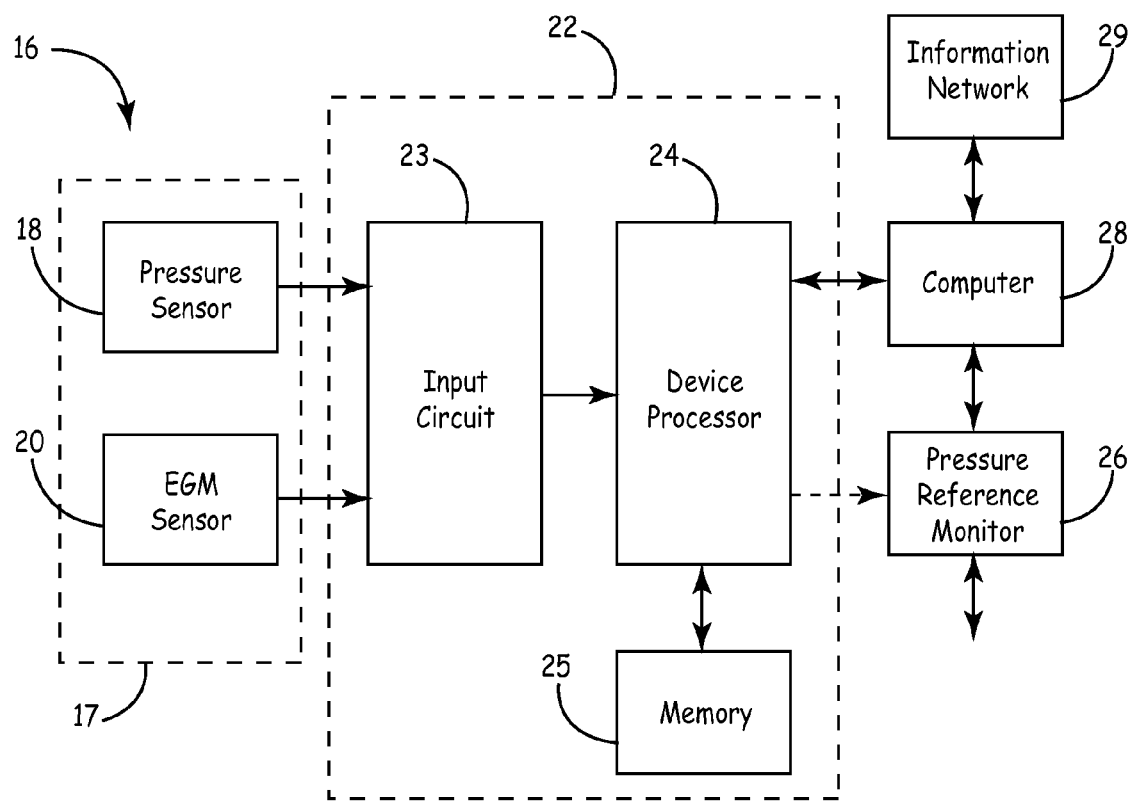
FIG. 1 is a block diagram of a cardiovascular analysis system.

FIG. 1 is a block diagram of cardiovascular analysis system 16, which senses hemodynamic pressures in a patient's heart and analyzes sensed hemodynamic pressure data to assess health conditions of the patient. System 16 includes sensor lead 17 (carrying hermetically sealed pressure sensor 18 and electrogram (EGM) sense electrode 20), implantable hemodynamic monitor (IHM) 22 (including input circuit 23, device processor 24 and memory 25, atmospheric pressure reference monitor (PRM) 26, computer 28, and information network 29.

In one embodiment, the IHM 22 is a CHRONICLE® Model 9520 IHM, described in commonly assigned U.S. Pat. No. 5,368,040. In other embodiments, hemodynamic data can be sensed and recorded by an IMD that also functions as a pacemaker, cardioverter, defibrillator, and/or drug pump. The sensor lead 17 can be a Medtronic® Model 4328A, and the PRM 26 can be a Medtronic® Model 2955HF, both available from Medtronic, Inc., Minneapolis, Minn. Computer 28 can be a Medtronic® Model 9790 programmer or a PC with CHRONICLE® software.

Hemodynamic data can include indicators of mechanical heart function, for example, hemodynamic pressures at various cardiovascular locations, such as in the right ventricle, left ventricle, right atrium, left atrium, pulmonary arteries, and systemic arteries. Input circuit 23 is a signal processing circuit that receives a pressure signal representative of blood pressures in the heart (e.g., in the right ventricle) from pressure sensor 18 and an electrical signal representative of the electrical activity of the heart from EGM sensor 20. Input circuit 23 may sample, demodulate or otherwise process the signals received from pressure sensor 18 and EGM sensor 20.

Device processor 24 derives hemodynamic pressure waveform data and hemodynamic parameters from the processed pressure and electrical signals received from input circuit 23. The hemodynamic waveform data and hemodynamic parameters are stored in memory 25 on a beat-by-beat basis, minute-to-minute basis, hour-to-hour basis, or on some other basis.

Because IHM 22 senses absolute blood pressure values, the patient is also provided with externally worn PRM. Contemporaneous atmospheric pressure values produced by PRM 26 are communicated to computer 28 along with data from IHM 22.

Computer 28 accumulates trend data that is stored in a memory at a programmable resolution. System 16 can be connected to information network 29, which includes an Internet-accessible database of cardiovascular information obtained using system 16. Information network 29 can be used to provide patient information to computers and medical personnel located remotely from the patient.

In operation, when accumulating hemodynamic data, it is possible for undesirable artifactual data to be recorded by system 16. Artifactual data is problematic, because unidentified artifactual data represents unreliable, aberrant data in a hemodynamic data set and can affect analyses of health conditions. System 16 analyzes hemodynamic waveform data to detect, identify and handle artifactual data that may be present. Once identified, artifactual data can be labeled, excluded from stored hemodynamic waveform data, or otherwise identified or adjusted. This analysis and handling can be performed at various locations in system 16, such as at IHM 22, at computer 28, and at a processing node on information network 29.

Figure 2:
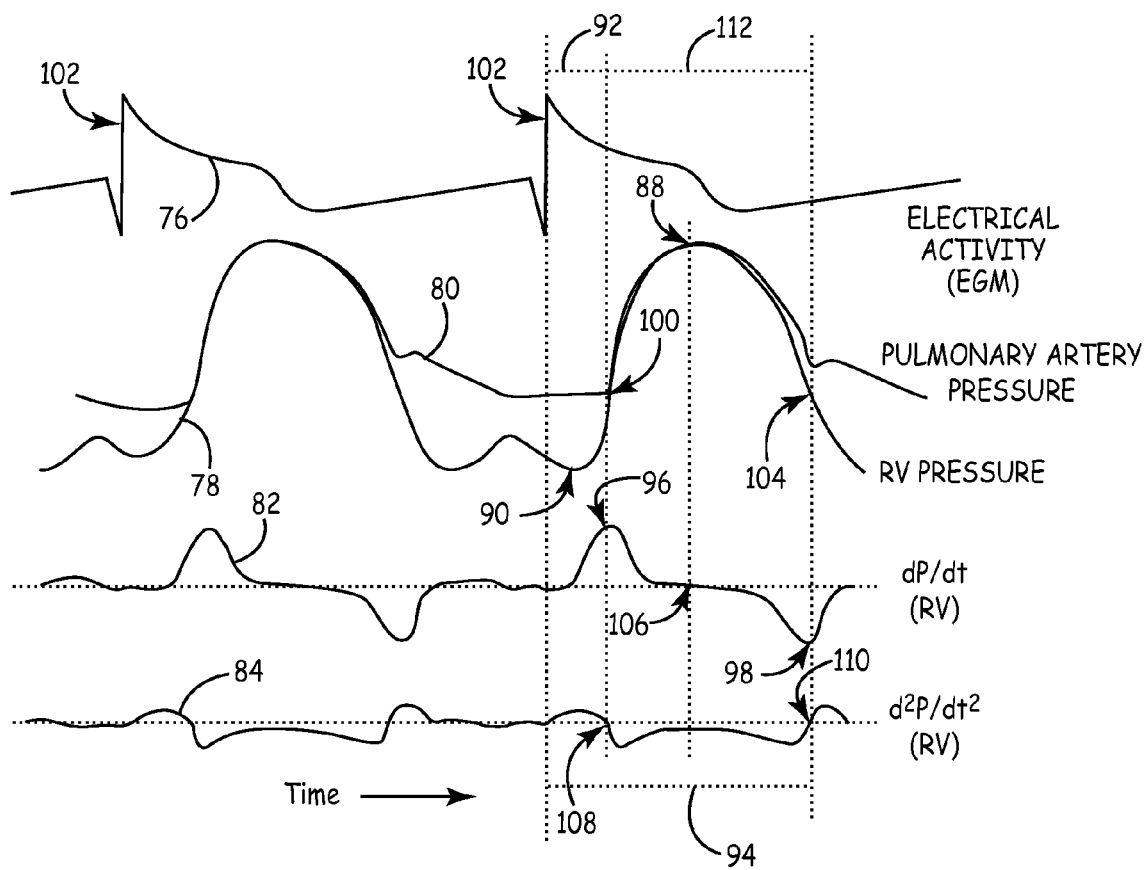
FIG. 2 is a diagram showing examples of waveforms of cardiovascular data obtainable from the cardiovascular analysis system of FIG. 1.

FIG. 2 is a diagram showing examples of waveforms of cardiovascular data obtainable from system 16. The waveforms relate to, without limitation, electrical activity (i.e., EGM) 76, right ventricle (RV) pressure 78, pulmonary artery pressure 80, the first derivative (dP/dt) of RV pressure 82, and the second derivative (d2P/dt2) of RV pressure 84. Hemodynamic parameters are sampled at a sampling rate of about 256 samples per second (256 Hertz), digitized and stored in memory registers. The data can be stored as waveforms by system 16.

IHM 22 is programmed to sense and calculate, for example, RV systolic pressure 88 (i.e., a maximum or peak pressure in a sampling window), RV diastolic pressure 90 (i.e., a first pressure sample in a sampling window), pulse pressure (where pulse pressure=RV systolic pressure–RV diastolic pressure), pre-ejection interval (PEI) 92, systolic time interval (STI) 94, peak positive change in pressure dP/dtmax 96 (synonymously called +dP/dtmax), peak negative change in pressure dP/dtmin 98 (synonymously called –dP/dtmax), estimated pulmonary artery diastolic pressure (ePAD) 100, R-waves 102, patient activity level, and heart rate. Other waveform parameters can be obtained, such as inflection point 104 corresponding to the closing of the pulmonary valve, point 106 where the dP/dt 82 first reaches a negative value, and points 108 and 110 where the d2P/dt2 84 becomes negative and then becomes positive again. Pulse width 112, measured between dP/dtmax 96 and dP/dtmin 98, is also identified.

Additional cardiovascular information can be derived from the hemodynamic values identified above. For instance, times at which the pulmonary valve opens and closes during a cardiovascular pulse cycle can be estimated as times 96 and 98 when dP/dtmax and dP/dtmin occur, respectively.

Figure 3:
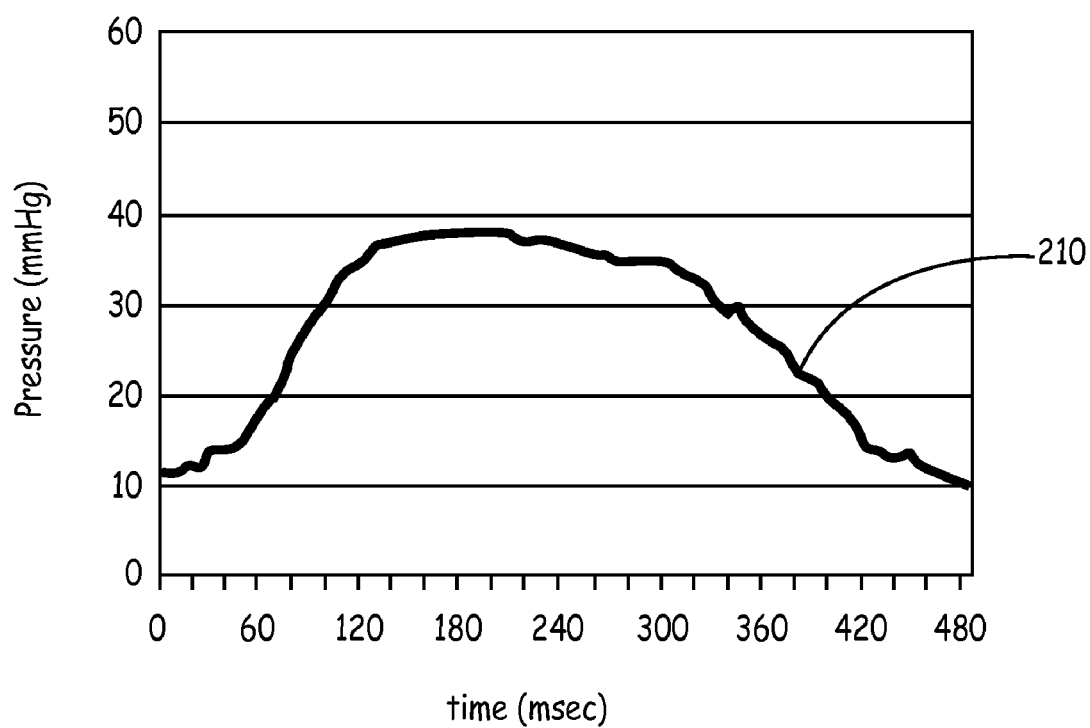
FIG. 3 is a graph of a hemodynamic pressure waveform for a cardiovascular pulse cycle.

FIG. 3 is a graph of hemodynamic pressure waveform 200 for a cardiovascular pulse cycle. Cardiovascular data samples are generally taken in a sampling window corresponding to a cardiovascular pulse cycle. That sampling window is a time interval for hemodynamic sensing of approximately 500 milliseconds (ms) that begins following electrical activation of the heart. In one embodiment, IHM 22 is programmed so that sampling windows occur every four days during times when a patient's activity levels are low (e.g., when sleeping). Sampling windows can occur at any other desired periodicity. In addition, periods of increased sampling resolution can be activated, such as while an acute event relating to cardiovascular health is occurring.

There are a number of general categories or groups of artifacts in hemodynamic pressure waveforms that can be detected and identified by system 16. These categories include spiky artifacts, drift artifacts, clipping artifacts, respiratory-related artifacts, and other artifacts. These categories of artifactual data are each discussed in turn.

Figure 4:
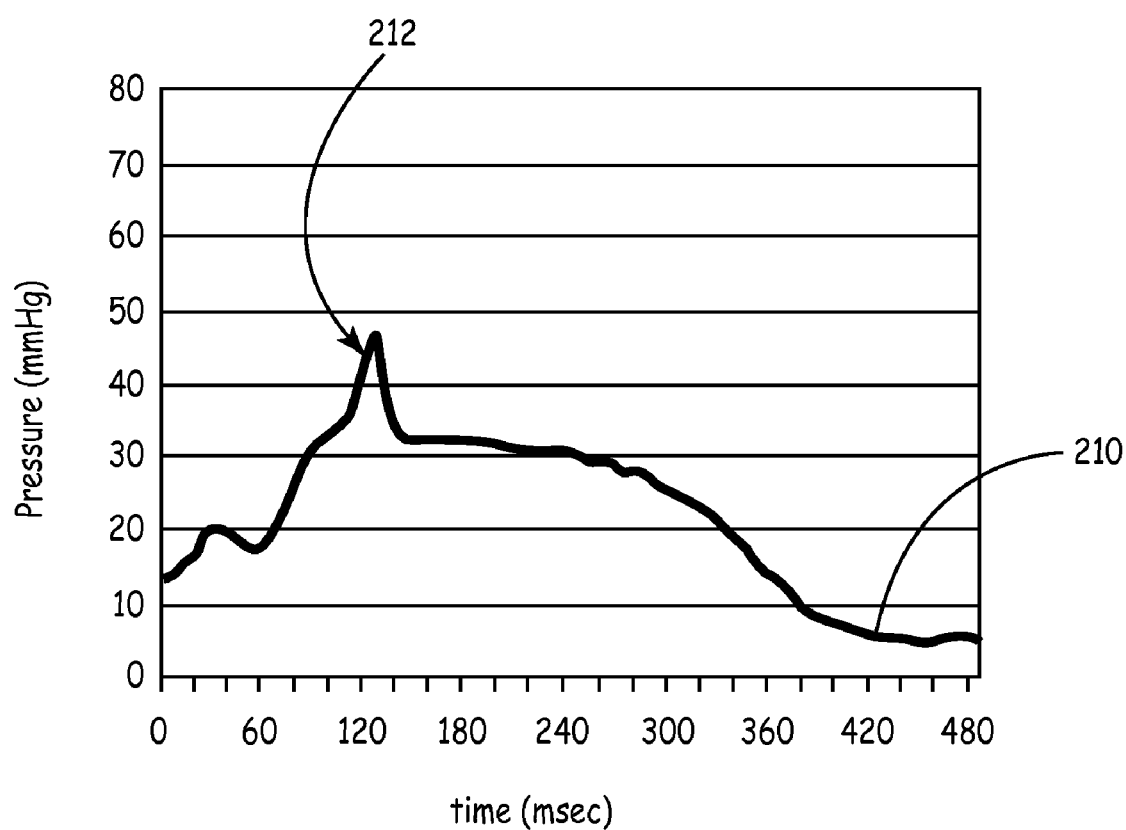
FIG. 4 is a graph of a hemodynamic pressure waveform containing spiky artifactual data.

FIG. 4 shows hemodynamic pressure waveform 210 containing spiky artifactual data that is represented, at least in part, at region 212. Spiky artifacts in a hemodynamic pressure waveform generally correspond to relatively large changes in pressure over relatively short periods of time. Region 212 of waveform 210 corresponds to a relatively large change in pressure (about 10 mmHg) over a relatively short period of time (about 10 msec), which indicates spiky artifactual data.

There are numerous causes of spiky artifacts. It is possible that a spiky artifact will appear in a hemodynamic pressure waveform if sensor lead 17 is improperly placed in the heart. Moreover, if sensor lead 17 is loosened, it may move or "whip" within the right ventricle during systole and produce a narrow-width, high pressure spike in a corresponding hemodynamic pressure waveform. Also, possible contact (e.g., bumping, bouncing, banging, and sustained contact) between sensor lead 17 and inner tissue or valves of the heart increases a likelihood that a spiky artifact will appear during waveform capture. The amplitude of the spike may vary depending on an extent of sensor lead 17 dislodgement or contact with tissue of the heart. Spiky artifacts tend to affect all hemodynamic parameters sensed by IHM 22, except diastolic pressure (Pdias). Spiky artifacts generally increase systolic pressure (Psys), ePAD, PEI, dP/dtmax, and dP/dtmin values, which can produce a cumulative increase in trend data obtained from a series of hemodynamic pressure waveforms. In addition, spiky artifacts generally decrease STI values, with corresponding effects on trend data. The spiky artifactual data shown in FIG. 4 is significant enough to affect hemodynamic pressure waveform parameters such as Psys, pulse pressure (Ppulse), ePAD, dP/dtmax, dP/dtmin, PEI and STI.

Certain criteria can be used by system 16 to detect spiky artifacts in hemodynamic pressure waveforms. Hemodynamic pressure waveforms having a dP/dtmax greater than a predetermined value are identified as likely containing spiky artifactual data. That predetermined value can be a generalized value, such as about 512 mmHg/sec, or can be a value individualized for the patient, such as a value determined based upon previously-gathered non-artifactual patient data. In addition, any hemodynamic pressure waveform having a pulse width less than a predetermined value, such as about 74.2 milliseconds (msec) or a patient-specific value, are identified as likely containing spiky artifactual data.

Figure 5:
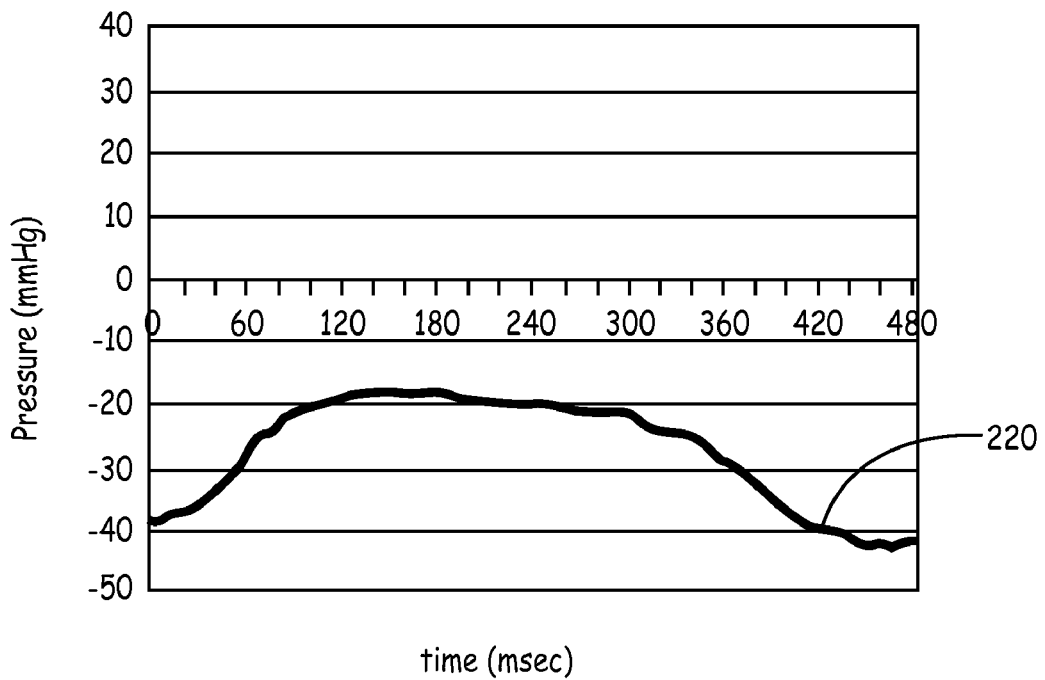
FIG. 5 is a graph of a hemodynamic pressure waveform containing downward drift artifactual data.
Figure 6:
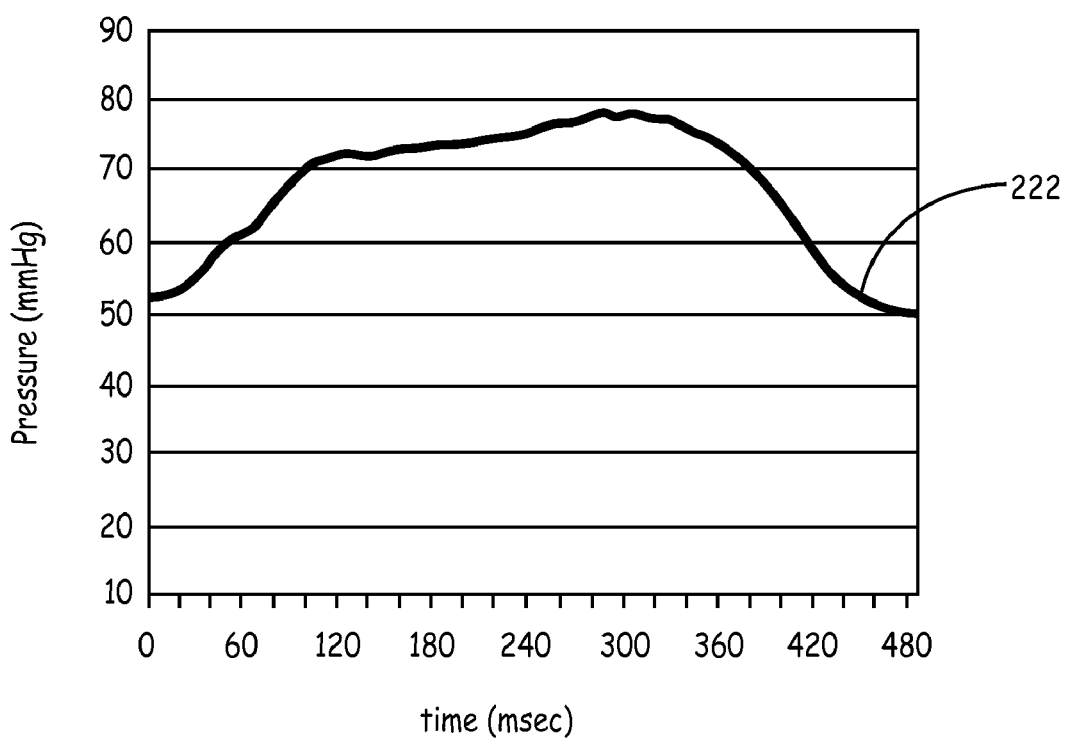
FIG. 6 is a graph of a hemodynamic pressure waveform containing upward drift artifactual data.

FIGS. 5 and 6 are representations of hemodynamic pressure waveforms 220 and 222 containing drift artifactual data. Waveforms containing drift artifacts generally have shapes that appear normal, but quantitative values of hemodynamic pressure parameters are too high or too low to be credible. Drift artifacts result in a shift from normal hemodynamic pressure values, and can be downward or upward. Hemodynamic pressure waveform 220, shown in FIG. 5, relates to downward drift artifactual data, and hemodynamic pressure waveform 222, shown in FIG. 5, relates to upward drift artifactual data. Pressure values of hemodynamic pressure waveform 220 shown in FIG. 5 have negative values, which indicates the presence of artifactual data. In FIG. 5, pressure values of hemodynamic pressure waveform 222 are all greater than or equal to about 50 mmHg, which indicates the presence of artifactual data.

Downward drift artifactual data, such as that shown in FIG. 5, can occur for a number of reasons including, without limitation, non-physiological causes such as sensor failure and a patient traveling to a high altitude location (i.e., a low atmospheric pressure location) without PRM 26. Sensor failure can occur when sensor lead 17 begins to lose hermaticity, which can be reflected in a hemodynamic pressure waveform with pressure values that decrease to a zero value. Traveling without PRM 26 affects hemodynamic pressure values because IHM 22 records absolute pressure values, and trend data from a series of hemodynamic pressure waveforms is affected by changes in atmospheric pressure in the absence of proper atmospheric correction using data from PRM 26. When downward drift artifacts occur, ePAD, Psys, Pdias, and Ppulse values generally decline, whereas dP/dtmax, dP/dtmin, PEI and STI values generally remain unaltered.

Artifacts caused by a patient traveling without PRM 26 will typically show an abrupt change in hemodynamic parameters. In contrast, sensor failure is a progressive event that normally takes a substantial number of days before hemodynamic parameters decline.

Non-physiological downward drift artifactual data can generally be identified where an average pressure value of a hemodynamic pressure waveform is negative (i.e., when the average pressure value is below zero mmHg) or below a value individualized for the patient. If overall values of a hemodynamic pressure waveform decrease gradually, a downward drift artifact is grouped as a sensor failure artifact. If an overall value of a hemodynamic pressure waveform decreases abruptly, a downward drift artifact is grouped as one induced by a patient traveling to high altitudes without PRM 26.

Upward drift artifactual data, such as that shown in FIG. 6, can occur, for example, when a patient travels to a low altitude location (i.e., a high atmospheric pressure location) without PRM 26. Upward drift artifacts generally cause an increase in ePAD, Psys, Pdias, and Ppulse values, and generally have no effect on dP/dtmax, dP/dtmin, PEI and STI values.

Non-physiological upward drift artifactual data can generally be identified where a hemodynamic pressure waveform has a Pdias value greater than a predetermined value, such as about 50 mmHg or a value individualized for the patient.

Figure 7:
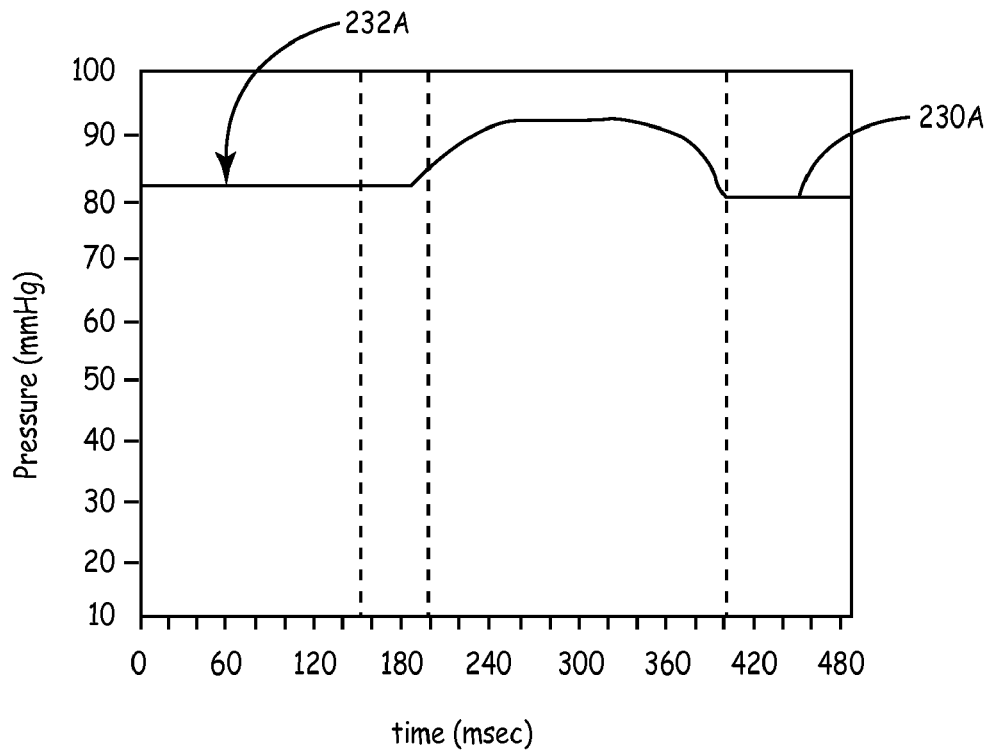
FIGS. 7 and 8 are graphs of hemodynamic pressure waveforms containing clipping artifactual data.
Figure 8:
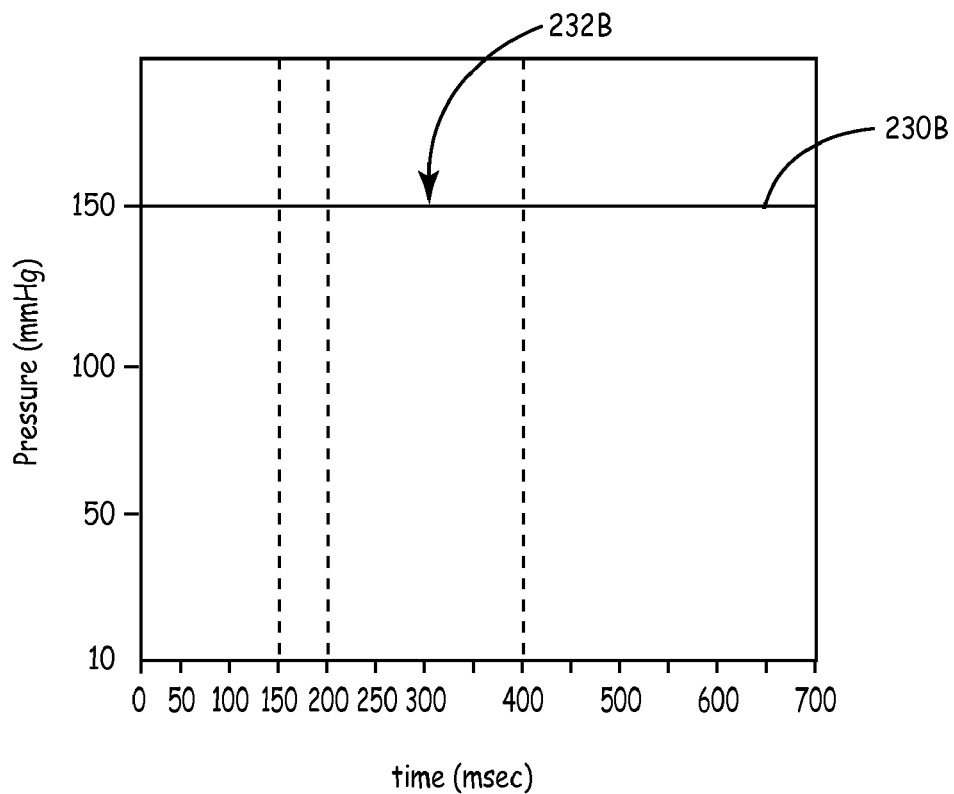

FIGS. 7 and 8 are representations of hemodynamic pressure waveforms 230A and 230B containing clipping artifacts. Hemodynamic pressure waveforms containing clipping artifacts are generally characterized as having substantially constant pressure values through one or more intervals of waveform data collection. Typically, IHM 22 is programmed to sense pressure data at a certain range of atmospheric pressures (e.g., from 700 to 760 mmHg). If a patient travels to either an extremely high or extremely low altitude location, the atmospheric pressure may be outside the programmed range of IHM 22. Atmospheric pressure reference data from PRM 26 typically cannot overcome the problem of exceeding the programmed range of IHM 22. Clipping artifacts result from reaching an upper or lower threshold of pressure sensing for IHM 22. In that way, clipping artifacts are distinguishable from drift artifacts because clipping artifacts cause a significant change in a shape of hemodynamic waveforms, unlike drift artifacts. Clipping artifacts can significantly affect ePAD, Psys, Pdias, Ppulse, dP/dtmax, dP/dtmin, PEI and STI values.

Because clipping artifacts can occur regardless of use of PRM 26, deviations in hemodynamic parameters due to clipping artifacts can be large. Indeed, because PRM 26 typically has a far greater capture range than IHM 22, PRM 26 can accurately record atmospheric pressure while IHM 22 simultaneously overestimates hemodynamic pressure values.

Clipping artifacts can be identified where a hemodynamic pressure waveform has a substantially constant pressure value for longer than a predetermined time during a designated period of pressure sensing is categorized as containing artifactual data. For instance, hemodynamic pressure waveforms having a substantially constant pressure value for longer than about 78 msec during the first 150 msec of pressure sensing for a cardiac pulse cycle (see, e.g., region 232A in FIG. 7) can be categorized as containing clipping artifactual data. Also, hemodynamic pressure waveforms having a substantially constant pressure value for longer than about 150 msec during a period from about 200 msec to about 400 msec of pressure sensing for a cardiac pulse cycle (see, e.g., region 232B in FIG. 8) can be categorized as containing clipping artifactual data. Alternatively, clipping artifactual data can be identified based upon the presence of a substantially constant pressure value for intervals that are patient-specific.

Figure 9B:
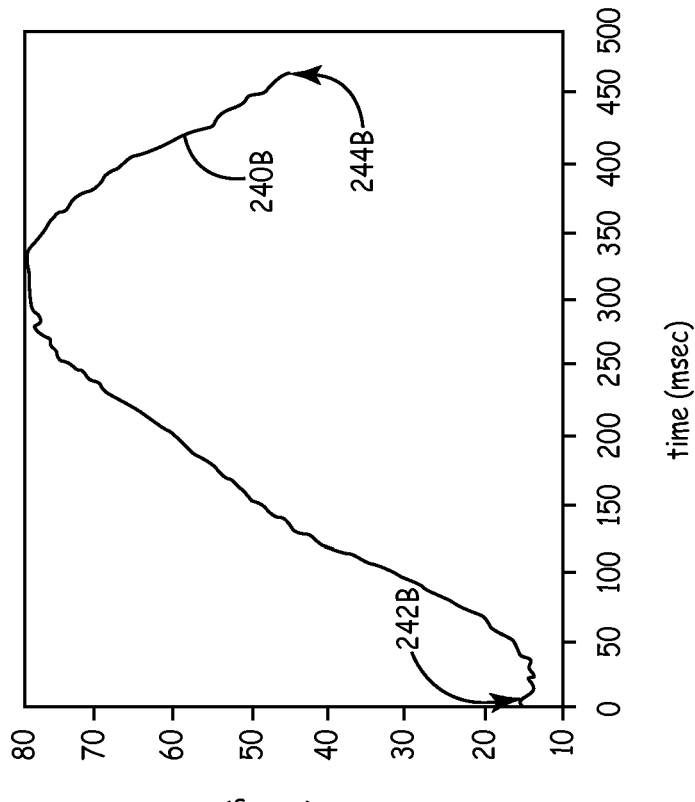
FIGS. 9A and 9B are graphs of hemodynamic pressure waveforms containing respiratory-related artifactual data.
Figure 9A:
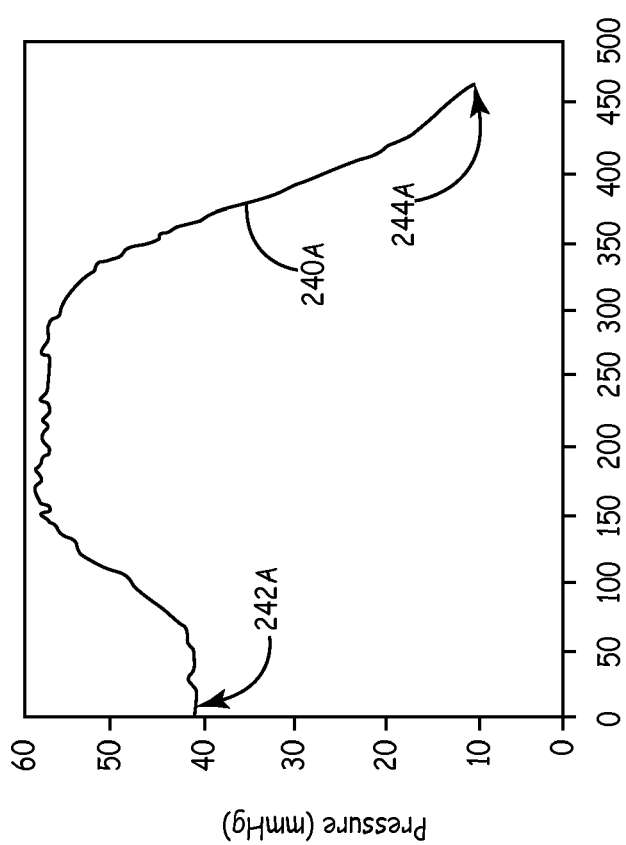

FIGS. 9A and 9B represent hemodynamic pressure waveforms 240A and 240B containing respiratory-related artifacts. Respiration cycles can cause baseline fluctuations in hemodynamic pressure waveforms. In general, respiration causes a cycling of intrathoracic pressures in patient's chest, which in turn affects hemodynamic pressures, such as those in the heart H. In addition, respiratory disturbances, such as coughing, yawning and snoring, can lead to artifactual data in hemodynamic pressure waveforms.

For example, respiration produced significant baseline fluctuations between first samples 242A and 242B and last samples 244A and 244B in the hemodynamic pressure waveforms shown in FIGS. 9A and 9B. In FIG. 9A, first sample 242A has a significantly greater pressure value than last sample 244A, by a difference of about 30 mmHg. The relatively high first sample 242A is due to exhalation, which generally causes an increase in intrathoracic pressure. In FIG. 9B, last sample 244B has a significantly greater pressure value than first sample 242B, by a difference of about 30 mmHg. The relatively low first sample 242B is due to inhalation, which generally causes a decrease in intrathoracic pressure.

Respiratory-related artifactual data can be identified where a first sample and a last sample of a sampling window of a hemodynamic pressure waveform for a cardiovascular pulse cycle have pressure values that differ by more than a predetermined value, such as about 30 mmHg or a value individualized for the patient.

Respiratory-related artifactual data is not necessarily erroneous data. However, when analyzing hemodynamic waveform data for a particular cardiovascular pulse cycle in isolation, unidentified respiratory-related artifactual data can distort hemodynamic parameters.

Other artifactual data may be present in hemodynamic pressure waveforms. For instance, artifactual data can result from conditions affecting pressure sensor 18, such as contact with valves or tissues of the heart. Moreover, tissue overgrowth over sensor 18 can affect hemodynamic pressure parameters derived by IHM 22. These other types of artifactual data may or may not manifest themselves in ways similar to the categories of artifacts previously discussed, but still result in unreasonable deviations from reasonable hemodynamic pressure waveform parameters. They are identified by detecting significant deviations from normal parameters.

Table 1 summarizes, by way of example and not by limitation, how selected artifact categories relate to selected hemodynamic parameters. Artifact categories that have a significant effect on particular hemodynamic parameters are marked "Yes", while hemodynamic parameters not significantly affected by those categories are marked "No".

TABLE 1

| Hemodynamic Parameter | Artifact Categories | | | | |
| --- | --- | --- | --- | --- | --- |
| | Spiky | Downward Drift | Upward Drift | Clipping | Respiratory-Related |
| ePAD | Yes | Yes | Yes | No | Yes |
| $P_{sys}$ | Yes | Yes | Yes | Yes | Yes |
| Pdias | No | Yes | Yes | Yes | Yes |
| Ppulse | Yes | Yes | No | Yes | Yes |
| dP/dtmax | Yes | No | No | Yes | No |
| dP/dtmin | Yes | Yes | No | Yes | No |
| PEI | Yes | No | No | Yes | No |
| STI | Yes | Yes | No | Yes | No |

System 16 detects and handles artifactual data in hemodynamic pressure waveforms by comparing characteristics of sensed waveforms to characteristics of waveforms known to be reliable. Once detected, system 16 can handle the artifactual data in a number of ways to increase a likelihood that only reliable hemodynamic data is used for any ultimate healthcare and research analyses for which the data was collected.

Figure 10:
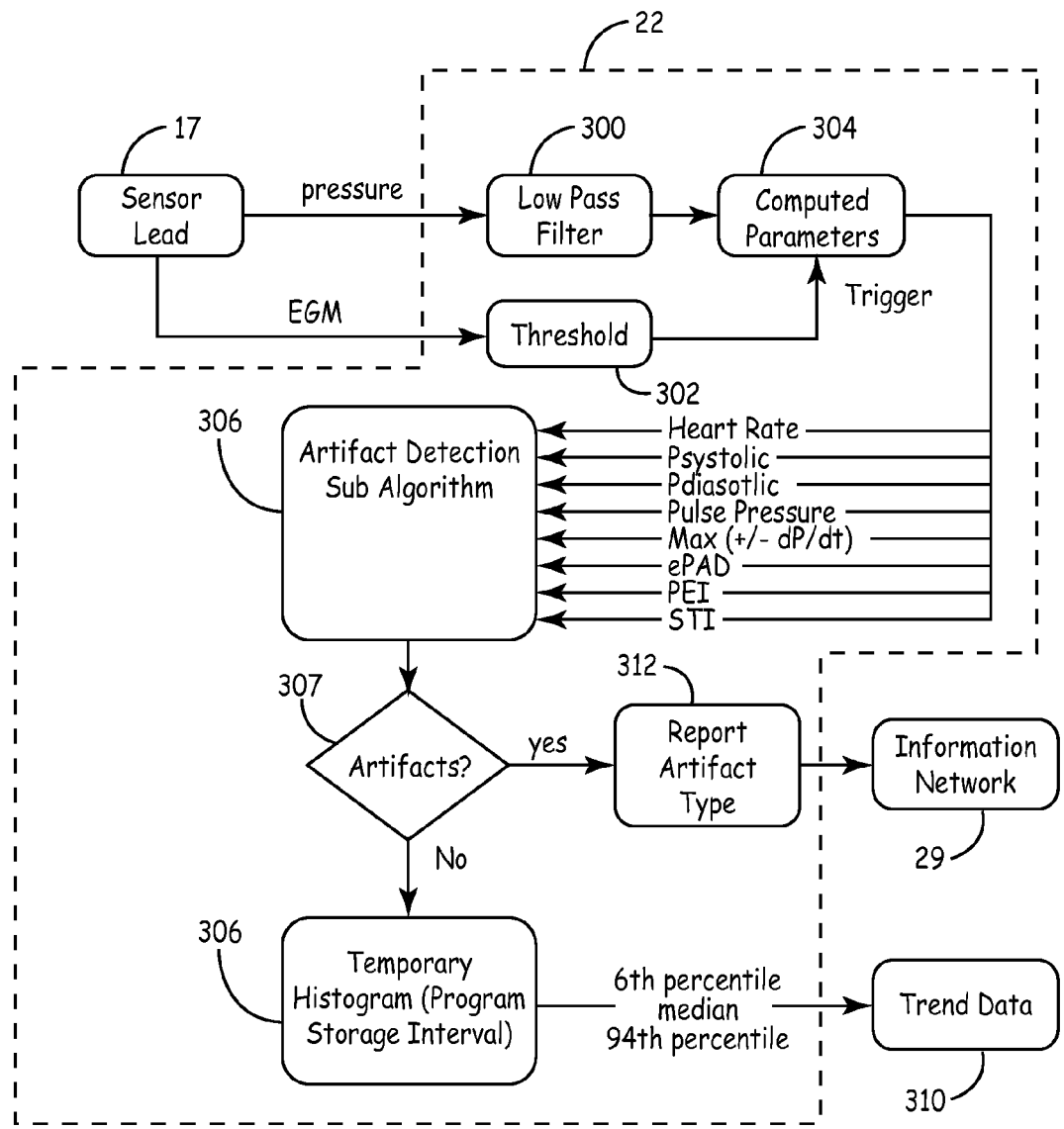
FIG. 10 is a flow chart of a device-level algorithm for identifying artifactual data in hemodynamic waveforms.

FIG. 10 is a flow chart of a device-level algorithm for identifying artifactual data in hemodynamic waveforms. As shown in FIG. 10, data analysis occurs within IHM 22. Sensor lead 17 produces a sensed pressure signal that is sent to low pass filter 300, and a sensed EGM signal that is analyzed by threshold detector 302 to trigger waveform capture (e.g., with a marker) following electrical activation of the heart. Other signal processing, such as demodulation, takes place, though not specifically shown in FIG. 10. The filtered pressure signal is sampled and digitized to produce pressure waveform data from which computed parameters 304 are calculated. Computed parameters 304 include any or all hemodynamic parameters corresponding to a recorded hemodynamic pressure waveform (e.g., heart rate, ePAD, Psys, Pdias, Ppulse, dP/dtmax, dP/dtmin, PEI and STI). This can include generating plots of first and second derivatives of the recorded hemodynamic pressure waveform. Range setup 305 is a determination of non-artifactual values for the parameters analyzed, and can include a determination of individualized, patient-specific values. Artifact detection sub-algorithm 306 analyzes hemodynamic pressure waveforms and corresponding hemodynamic parameters to determine whether or not artifactual data is present in each of the hemodynamic pressure waveforms (step 307). Sub-algorithm 306 can incorporate any or all of the criteria described above to detect spiky artifacts, drift artifacts, clipping artifacts, and respiratory-related artifacts. Sub-algorithm 306 operates as IHM-based software in the embodiment illustrated in FIG. 10.

If no artifacts are present in a hemodynamic pressure waveform, then the waveform data is sent to a temporary histogram 308, which collects hemodynamic data for a program storage interval (e.g., five minutes). Representative values of the hemodynamic data collected during the storage interval can then be communicated for storage in a database, for example. For each hemodynamic parameter, representative values can include values indicative of a range of values collected during the storage interval, such as a median value, a sixth percentile value, and a ninety-fourth percentile value. Waveform data (or representative values) are accumulated as trend data 310 for a series of hemodynamic pressure waveforms.

If artifacts are detected, then artifact types are reported 312. Information regarding the artifactual data (e.g., artifact type, and date and time of occurrence) is reported to information network 29, which can include a database and can incorporate Internet-based access features. Generally, only non-artifactual data is stored for analysis by information network 29.

Although artifact detection can occur within IHM 22, though limited battery life generally associated with IMDs raises a concern with conducting extensive processing operations with IHM 22. Therefore, where battery life of IHM 22 is a concern, it is preferred to analyze and process waveform data externally, where possible.

Figure 11:
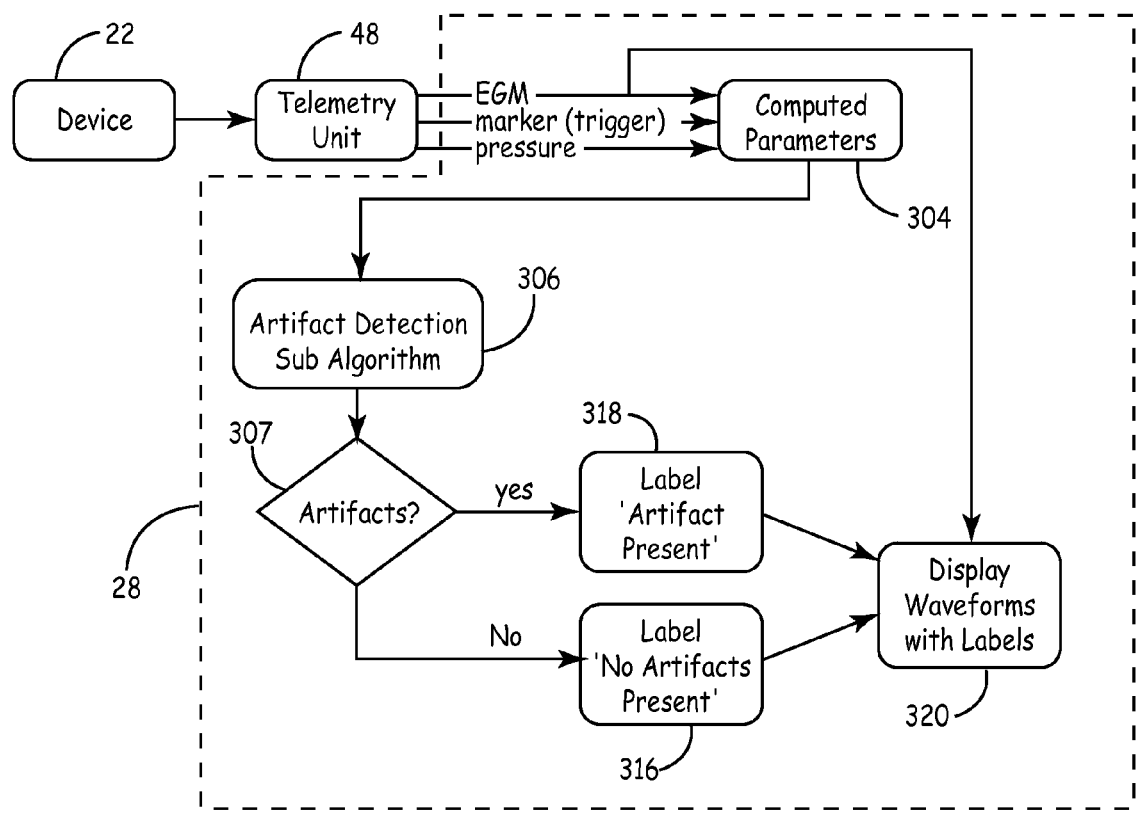
FIG. 11 is a flow chart of an external computer-level algorithm for identifying artifactual data in hemodynamic waveforms.

FIG. 11 is a flow chart of an external computer-level algorithm for identifying artifactual data in hemodynamic waveforms. In FIG. 11, analysis of hemodynamic pressure waveforms to detect artifactual data occurs in computer 28, externally of IHM 22. Cardiovascular data is gathered by IHM device 22 and is transmitted to a telemetry unit 48, which is operatively connected to computer 28. Computed parameters 304 are then calculated from the data transmitted by IHM 22, and range setup 305 is conducted. Computed parameters 304 are analyzed by artifact detection sub-algorithm 306, which is similar to that described with respect to FIG. 10.

If no artifacts are present in the waveform (step 307), then the waveform is labeled (step 316) (i.e., flagged, marked or otherwise identified) as having no artifacts present. If an artifact is detected (step 307), then the waveform is labeled (step 318) as having an artifact present. Labeled waveform data can be stored in a database, and can be displayed with labels that indicate the presence of any artifacts (step 320).

Analysis of waveforms in computer 28 can be accomplished using commercially available software such as MATLAB software, available from Mathworks, Inc., Natick, Mass. In other embodiments, analysis can be incorporated using custom software used in conjunction with CHRONICLE® software, available from Medtronic, Inc., Minneapolis, Minn.

Figure 12:
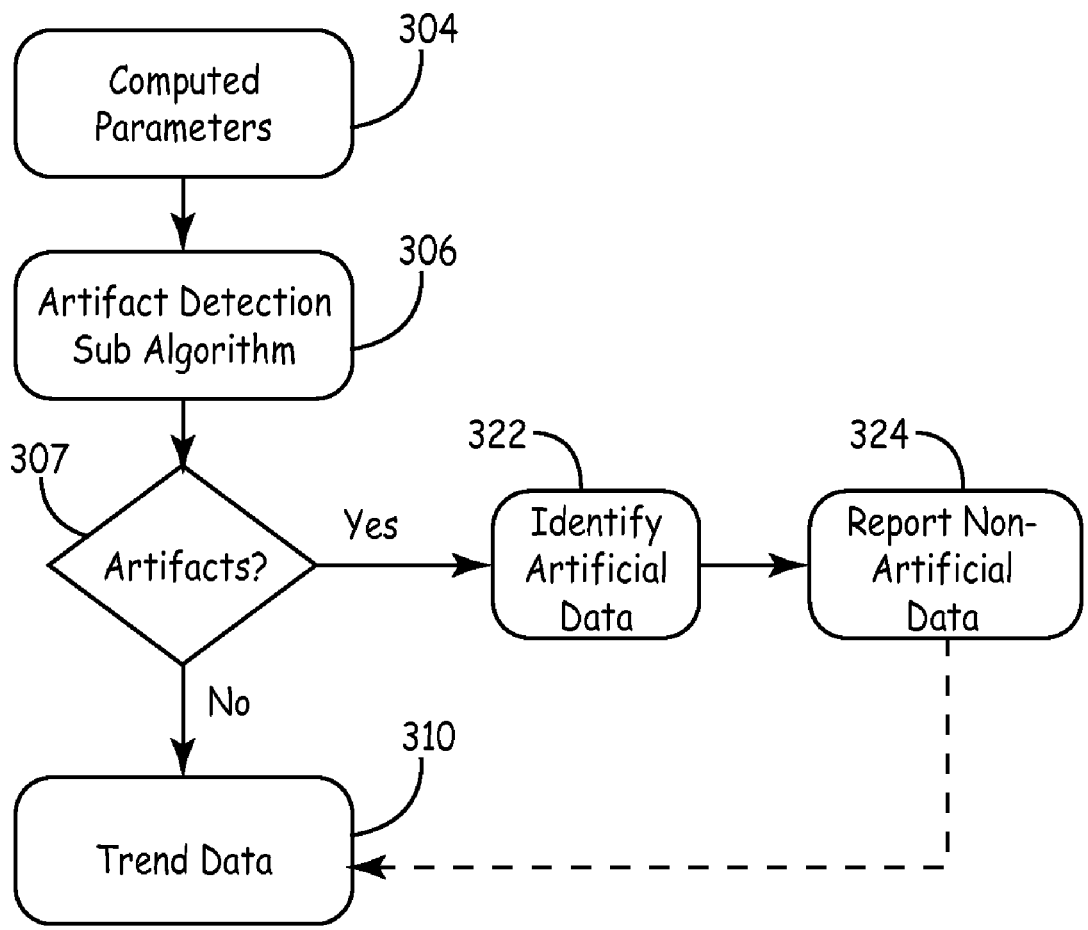
FIG. 12 is a flow chart of another algorithm for identifying artifactual data in hemodynamic waveforms.

FIG. 12 is a flow chart of another algorithm for identifying artifactual data in hemodynamic waveforms. In FIG. 12, detection artifactual data can occur in IHM 22, in computer 28, or elsewhere within system 16. This embodiment is generally similar to those discussed above with respect to FIGS. 10 and 11 in generating computed parameters 304 and conducting range setup 305. In this embodiment, computed parameters 304 are analyzed with artifact detection sub-algorithm 306 to determine if artifactual data is present (step 307). Hemodynamic data determined not to contain artifactual data (step 307) is accumulated in trend data 310. Where the presence of artifactual data is detected (step 307), the portion representing artifactual data is identified (step 322) and only non-artifactual data is reported (step 324) for inclusion in the trend data 310 compiled from a series of waveforms. Because certain categories of artifacts affect only certain hemodynamic parameters, unaffected parameters are reported in trend data 310 while parameters affected by the presence of artifactual data are excluded.

Figure 13:
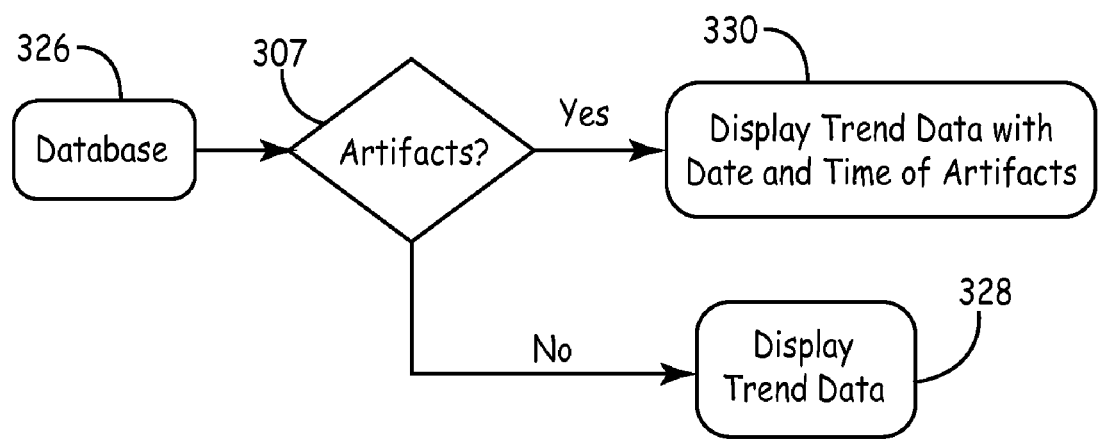
FIG. 13 is a flow chart of an information network-level algorithm for identifying artifactual data in hemodynamic waveforms.

FIG. 13 is a flow chart of an information network-level algorithm for identifying artifactual data in hemodynamic waveforms. In FIG. 13, detection of artifactual data occurs prior to storing data in database 326. Analysis of hemodynamic pressure waveforms to detect artifactual data can occur on any computer with access to information network 29. The algorithm shown in FIG. 13 can be used in conjunction with other processing algorithms, such as those shown and described with respect to FIGS. 10-12, to provide additional functionality not shown in FIG. 13.

Data from database 326 that does not contain artifacts can be displayed as trend data 328. Data containing artifacts can be displayed with indications as to the date and time of the artifactual data 330.

In addition to automated and computerized methods of artifact detection, visual inspection (i.e., manual inspection) of waveforms can be conducted. Visual inspection is conducted at a computer with access to information network 29 by looking at displayed individual waveforms to determine whether artifactual data is present.

By detecting and handling artifactual data that may be present in hemodynamic data sets (i.e., hemodynamic pressure waveforms), an increase in the reliability of cumulative trend data can be achieved. That is desirable in increasing reliability of diagnosis, monitoring, and treatment of cardiovascular conditions. Data that has been analyzed for the presence of artifactual data is more reliable for further analyses, and therefore the present invention can be used in conjunction with further cardiovascular data analysis processes, as desired.

Although the present invention has been described with reference to preferred embodiments, workers skilled in the art will recognize that changes may be made in form and detail without departing from the spirit and scope of the invention. For instance, while reference has been made to analysis of waveforms, it will be recognized that analysis of raw data corresponding to that represented in hemodynamic pressure waveforms can also be analyzed while remaining within the scope of the present invention.

We claim:

1. A system for hemodynamic waveform data trend analysis, the system comprising:
   means for generating hemodynamic pressure waveform data that corresponds to sensed hemodynamic pressure over time;
   means for analyzing the hemodynamic pressure waveform data to determine hemodynamic waveform parameters, including a systolic pressure and a diastolic pressure for a cardiovascular pulse cycle; and
   means for identifying multiple types of artifactual data in a series of hemodynamic waveforms based upon hemodynamic waveforms in the series and for generating trend data using hemodynamic waveforms containing the identified types of artifactual data, using only those of the hemodynamic parameters that are unaffected by the identified artifactual data.

2. A system according to claim 1 and further comprising means for excluding from the trend data any hemodynamic pressure waveform data for a cardiovascular pulse cycle containing artifactual data.

3. A system according to claim 1 and further comprising means for excluding artifactual data from hemodynamic waveform data containing the artifactual data.

4. A system according to claim 1 and further comprising means for creating dP/dt plots representative of the first derivatives of the hemodynamic pressure waveform data with respect to time, and determining maximum and minimum values for each dP/dt plot.

5. A system according to claim 4, wherein the artifactual data corresponds to any maximum dP/dt value greater than a predetermined value.

6. A system according to claim 5, wherein the predetermined value has a magnitude of about 512 mmHg/sec.

7. A system according to claim 1, wherein hemodynamic pressure waveform data having a pulse width less than a predetermined time period are identified as containing artifactual data.

8. A system according to claim 7, wherein the predetermined time period has a magnitude of about 74.2 milliseconds.

9. A system according to claim 1, wherein hemodynamic pressure waveform data having a negative average pressure value is identified as containing artifactual data.

10. A system according to claim 1, wherein hemodynamic pressure waveform data having a diastolic pressure value greater than a predetermined value is identified as containing artifactual data.

11. A system according to claim 10, wherein the predetermined value is about 50 mmHg.

12. A system according to claim 1, wherein hemodynamic pressure waveform data having a substantially constant pressure value for longer than a predetermined time during a designated period of pressure sensing is identified as containing artifactual data.

13. A system according to claim 12, wherein the predetermined time is about 78 milliseconds, and wherein the designated period of pressure sensing is from about zero to about 150 milliseconds of pressure sensing.

14. A system according to claim 12, wherein the predetermined time is about 150 milliseconds, and wherein the designated period of pressure sensing is from about 200 to about 400 milliseconds of pressure sensing.

15. A system according to claim 1, wherein the hemodynamic pressure waveform data includes a first sample and a last sample, and wherein any hemodynamic pressure waveform data having first and last samples with pressure values that differ by more than a predetermined value are identified as containing artifactual data.

16. A system according to claim 15, wherein the predetermined value is about 30 mmHg.

\* \* \* \* \*